United States Patent
Suehira

(10) Patent No.: US 10,255,661 B2
(45) Date of Patent: Apr. 9, 2019

(54) OBJECT INFORMATION ACQUIRING APPARATUS AND IMAGE PROCESSING METHOD

(71) Applicant: CANON KABUSHIKI KAISHA, Tokyo (JP)

(72) Inventor: Nobuhito Suehira, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 766 days.

(21) Appl. No.: 14/730,603

(22) Filed: Jun. 4, 2015

(65) Prior Publication Data
US 2015/0359519 A1 Dec. 17, 2015

(30) Foreign Application Priority Data

Jun. 11, 2014 (JP) ................... 2014-120292

(51) Int. Cl.
*A61B 8/08* (2006.01)
*G06T 5/00* (2006.01)
(Continued)

(52) U.S. Cl.
CPC ............ *G06T 5/002* (2013.01); *A61B 8/0825* (2013.01); *A61B 8/403* (2013.01); *A61B 8/4209* (2013.01);
(Continued)

(58) Field of Classification Search
CPC ......... A61B 8/0825; A61B 8/14; A61B 8/403; A61B 8/4209; A61B 8/4281;
(Continued)

(56) References Cited

U.S. PATENT DOCUMENTS

| 2004/0210137 A1 | 10/2004 | Baba et al. ................... 600/443 |
| 2010/0007894 A1 | 1/2010 | Suehira ......................... 356/497 |
| 2013/0208964 A1* | 8/2013 | Dwivedi .................. G06K 9/34 382/128 |

FOREIGN PATENT DOCUMENTS

| JP | 4-236952 A | 8/1992 |
| JP | 2003-070786 | 3/2003 |

(Continued)

OTHER PUBLICATIONS

T. Loupas et al., "An Adaptive Weighted Median Filter for Speckle Suppression in Medical Ultrasonic Images", *IEEE Transactions on Circuits and Systems*, vol. 36, No. 1, pp. 129-135 (Jan. 1989).

(Continued)

*Primary Examiner* — Michael T Rozanski
(74) *Attorney, Agent, or Firm* — Venable LLP

(57) ABSTRACT

An object information acquiring apparatus is used that includes: an ultrasound probe that receives an acoustic wave propagating from an object and outputs an electric signal; and a processor that generates an image of the inside of the object, using the electric signal. The processor creates a frequency distribution of pixel values included in a region of interest including a point of interest in the image, classifies the point of interest on the basis of the shape of the frequency distribution and the position of the point of interest in the frequency distribution, and determines a pixel value of the point of interest on the basis of a classification result of the point of interest.

11 Claims, 7 Drawing Sheets

(51) Int. Cl.
    *G06T 7/00* (2017.01)
    *G06T 15/08* (2011.01)
    *A61B 8/14* (2006.01)
    *A61B 8/00* (2006.01)
    *G06T 5/40* (2006.01)
    *G06K 9/62* (2006.01)

(52) U.S. Cl.
    CPC .......... *A61B 8/4461* (2013.01); *A61B 8/5223* (2013.01); *G06K 9/6212* (2013.01); *G06T 5/003* (2013.01); *G06T 5/007* (2013.01); *G06T 5/40* (2013.01); *G06T 7/0012* (2013.01); *A61B 8/14* (2013.01); *A61B 8/4281* (2013.01); *A61B 8/468* (2013.01); *A61B 8/469* (2013.01); *G06T 2207/10132* (2013.01); *G06T 2207/30096* (2013.01)

(58) Field of Classification Search
    CPC ....... A61B 8/4461; A61B 8/468; A61B 8/469; A61B 8/5223; G06K 9/6212; G06T 2207/10132; G06T 2207/30096; G06T 5/002; G06T 5/003; G06T 5/007; G06T 5/40; G06T 7/0012
    See application file for complete search history.

(56) References Cited

FOREIGN PATENT DOCUMENTS

| | | |
|---|---|---|
| JP | 2003-220058 A | 8/2003 |
| JP | 2006-340992 A | 12/2006 |
| JP | 2012-134576 A | 7/2012 |
| WO | 2009/060751 A1 | 5/2009 |

OTHER PUBLICATIONS

Office Action dated Oct. 2, 2018, in counterpart application JP 2015-116307 (6 pages).

\* cited by examiner

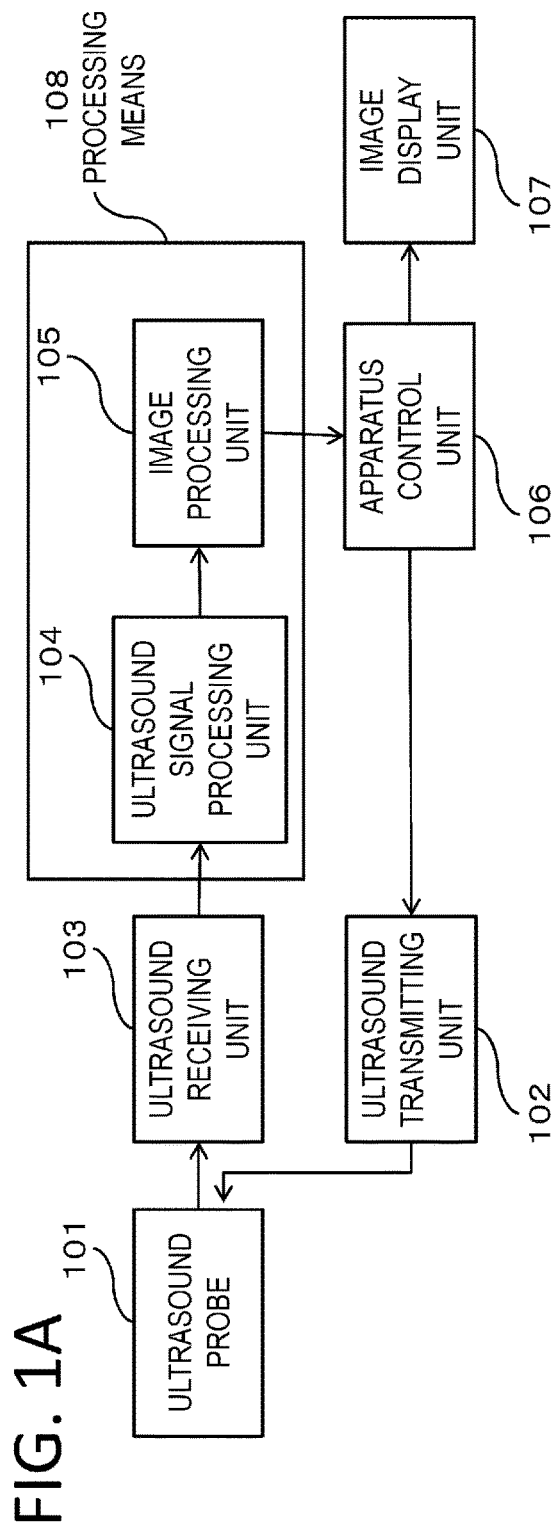
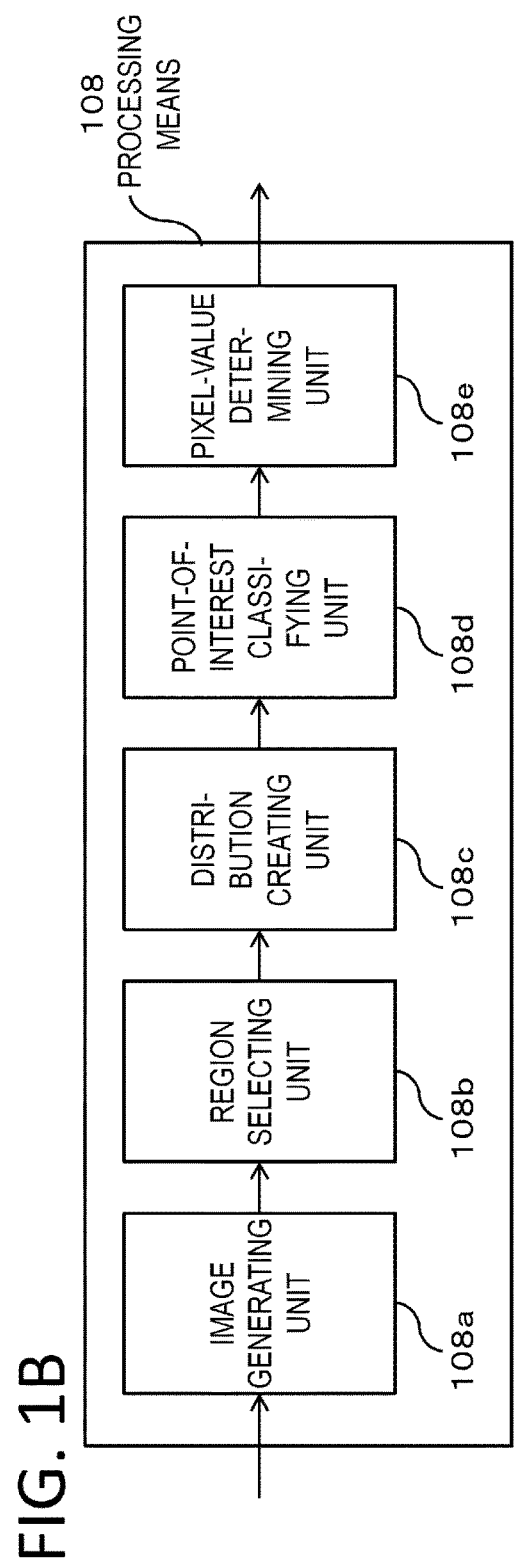

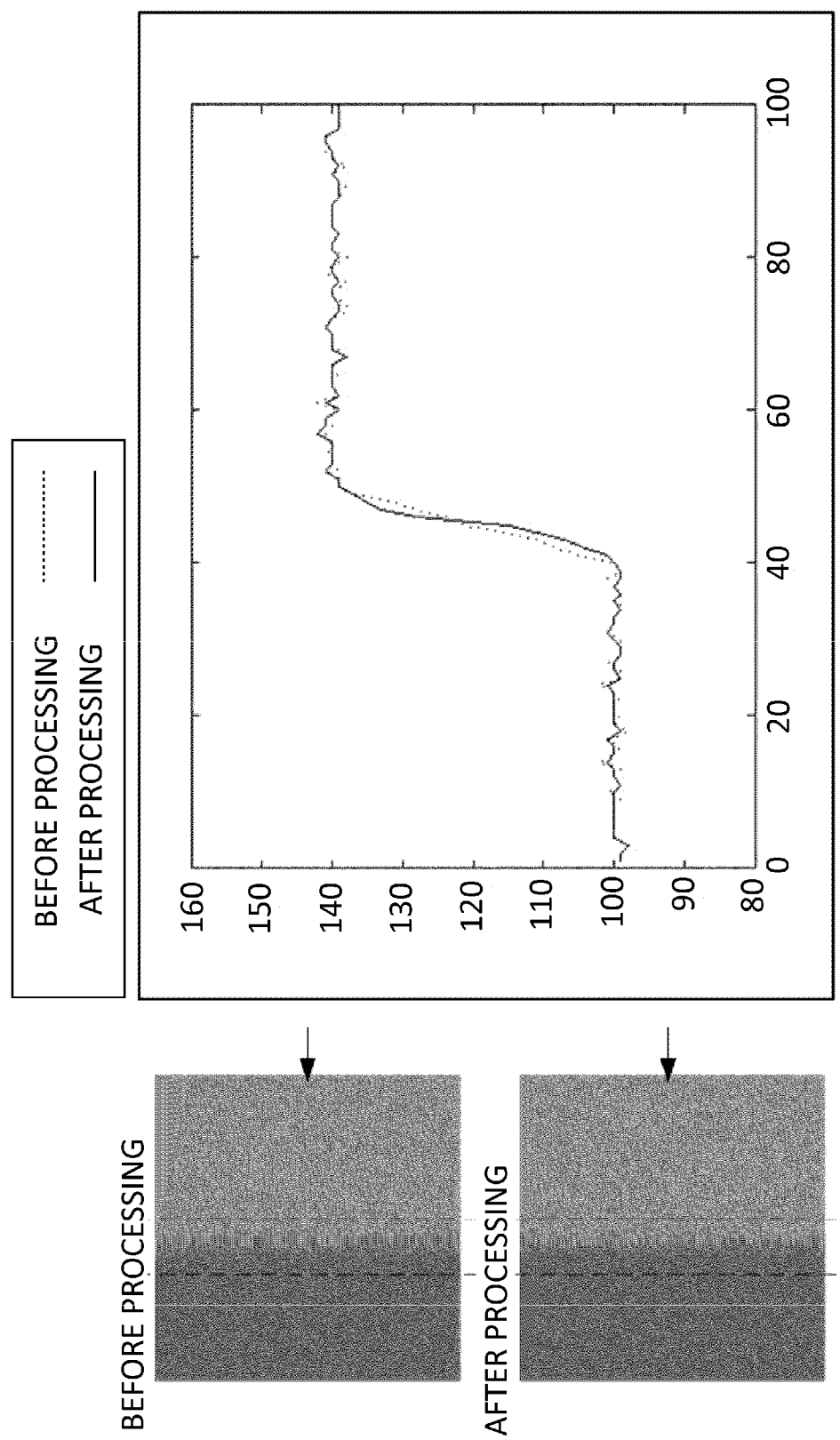

OBJECT INFORMATION ACQUIRING APPARATUS AND IMAGE PROCESSING METHOD

BACKGROUND OF THE INVENTION

Field of the Invention

The present invention relates to an object information acquiring apparatus and an image processing method.

Description of the Related Art

An ultrasound diagnostic apparatus radiates an ultrasound wave from an ultrasound probe into an object, receives the ultrasound wave reflected on a tissue of the object, and forms a tissue image of an organism. Since the ultrasound diagnostic apparatus is noninvasive to the organism, the ultrasound diagnostic apparatus is used in many medical fields. In an ultrasound image obtained by the ultrasound diagnostic apparatus, granular pattern noise called speckle noise sometimes occurs. The speckle noise is noise caused by interference of waves scattered by innumerable small reflectors in the object. The noise could be a hindrance to diagnosis. Therefore, it is desirable to reduce the noise as much as possible.

Japanese Patent Application Laid-Open No. 2003-070786 discloses a method of reducing speckle noise using spatial compound. In the spatial compound, an ultrasound wave is radiated at a plurality of angles. Therefore, for example, a measurement time increases and a burden on a patient increases.

As a method for reducing noise without increasing a measurement time, a reduction in noise by image processing is conceivable. "An adaptive weighted median filter for speckle suppression in medical ultrasonic images", IEEE Vol. 36, pp. 129-135 (1989) discloses a method of removing speckle noise using a median filter. However, an image filter for removing noise sometimes blurs even a structure and a microstructure. On the other hand, a Laplacian filter and a high-boost filter are known as a filter for emphasizing a structure. Since the filters use a difference or the like, even noise is sometimes emphasized. Therefore, there is a demand for processing that can emphasize a structure while suppressing noise.

Patent Literature 1: Japanese Patent Application Laid-Open No. 2003-070786

Non Patent Literature 1: "An adaptive weighted median filter for speckle suppression in medical ultrasonic images", IEEE Vol. 36, pp. 129-135 (1989)

SUMMARY OF THE INVENTION

The present invention has been devised on the basis of such problem recognition. It is an object of the present invention to perform image processing for emphasizing a structure while suppressing noise.

The present invention provides an object information acquiring apparatus comprising:

an ultrasound probe that receives an acoustic wave propagating from an object and outputs an electric signal; and a processor that generates an image of an inside of the object, using the electric signal, wherein the processor creates a frequency distribution of pixel values included in a region of interest including a point of interest in the image, classifies the point of interest on the basis of a shape of the frequency distribution and a position of the point of interest in the frequency distribution, and determines a pixel value of the point of interest on the basis of a classification result of the point of interest.

The present invention also provides an image processing method comprising:

an ultrasound receiving step for receiving an acoustic wave propagating from an object and outputting an electric signal;

an image generating step for generating an image of an inside of the object, using the electric signal;

a distribution creating step for creating a frequency distribution of pixel values included in a region of interest including a point of interest in the image;

a point-of-interest classifying step for classifying the point of interest on the basis of a shape of the frequency distribution and a position of the point of interest in the frequency distribution; and a pixel-value determining step for determining a pixel value of the point of interest on the basis of a classification result of the point of interest.

The present invention provides an image processing method comprising:

a distribution creating step for creating a frequency distribution of pixel values included in a region of interest including a point of interest in an image;

a point-of-interest classifying step for classifying the point of interest on the basis of a shape of the frequency distribution and a position of the point of interest in the frequency distribution; and a pixel-value determining step for determining a pixel value of the point of interest on the basis of a classification result of the point of interest.

According to the present invention, it is possible to perform image processing for emphasizing a structure while suppressing noise.

Further features of the present invention will become apparent from the following description of exemplary embodiments with reference to the attached drawings.

BRIEF DESCRIPTION OF THE DRAWINGS

FIGS. 1A and 1B are block diagrams of an ultrasound diagnostic apparatus in a first embodiment;

FIGS. 5A and 5B are processing examples of a step structure in the first embodiment;

DESCRIPTION OF THE EMBODIMENTS

Figure 2:
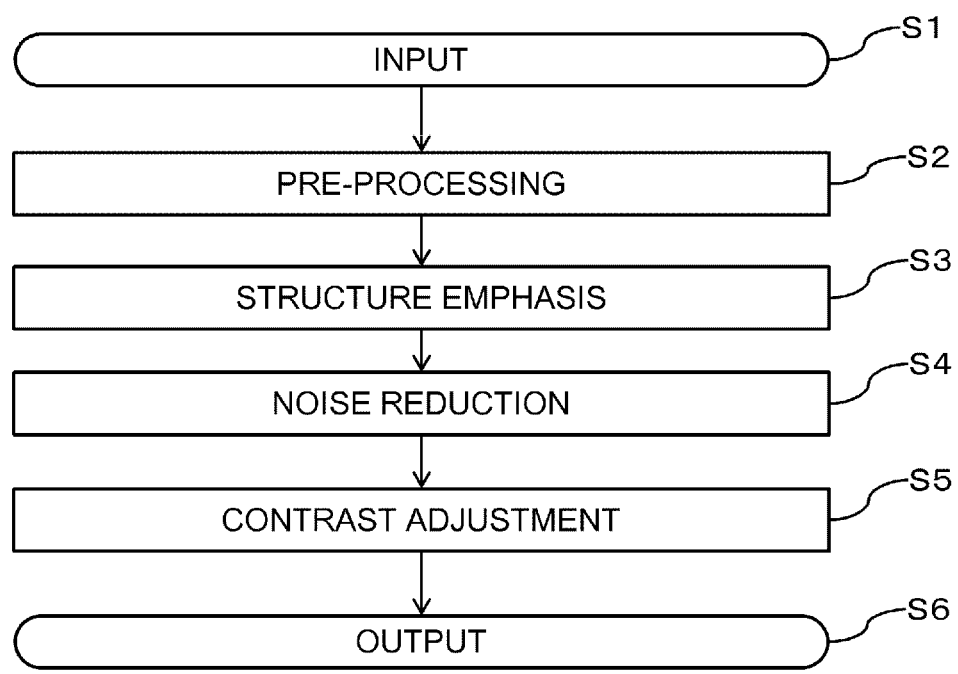
FIG. 2 is a flowchart of image processing in the first embodiment.

Preferred embodiments of the present invention are explained below with reference to the drawings. However, the dimensions, the materials, the shapes, a relative arrangement, and the like of components described below should be changed as appropriate according to the configuration and various conditions of an apparatus applied with the invention and are not meant to limit the scope of the present invention to the description below.

The present invention relates to an image processing method for emphasizing a structure while suppressing noise with respect to an image including fine noise such as a speckle noise. Therefore, the present invention is also grasped as an image processing apparatus or a control method for the image processing apparatus. The present invention can be used in, in particular, detecting an ultrasound wave propagating from an object, generating characteristic information inside the object, and imaging the characteristic information. Therefore, the present invention is grasped as an object information acquiring apparatus or a control method for the object information acquiring apparatus, an object information acquiring method, or a signal processing method. The present invention is also grasped as a computer program for causing an information processing apparatus including a hardware resource such as a CPU to execute these methods and a non-transitory storage medium having the computer program recorded therein.

The object information acquiring apparatus of the present invention includes an apparatus that makes use of an ultrasound echo technique for irradiating an ultrasound wave on an object and receiving (detecting), in a plurality of measurement positions, a reflected wave (an ultrasound echo) reflected in a portion where acoustic impedance changes in the object and propagating to the measurement positions. The object information acquiring apparatus obtains characteristic information of the inside of the object in a form of image data or the like on the basis of the reflected wave (the ultrasound echo). Therefore, the object information acquiring apparatus can be called ultrasound imaging apparatus or ultrasound image-forming apparatus. When a tissue of an organism is measured as the object, a generated image can be used for diagnosis for a medical purpose. Therefore, the object information acquiring apparatus may be called ultrasound diagnostic apparatus.

Characteristic information in the ultrasound diagnostic apparatus is information reflecting a change in acoustic impedance in the object. The information is displayed as image data. Therefore, a user can grasp a structure in the object. An ultrasound in the present invention includes an elastic wave called sound wave or acoustic wave. An electric signal converted from the acoustic wave by a probe (or an element in the probe) is referred to as acoustic signal.

First Embodiment (Apparatus Configuration)

An ultrasound diagnostic apparatus according to the present invention is briefly explained. FIG. 1A is a block diagram of the ultrasound diagnostic apparatus according to a first embodiment of the present invention. The ultrasound diagnostic apparatus according to the present invention includes an ultrasound probe 101, an ultrasound transmitting unit 102, an ultrasound receiving unit 103, an ultrasound-signal processing unit 104, an image processing unit 105, an apparatus control unit 106, and an image display unit 107.

As the ultrasound probe 101, a one-dimensional array oscillator made of PZT ceramic is used. The ultrasound probe 101 transmits a desired ultrasound wave to a test object on the basis of a signal received from the ultrasound transmitting unit 102. The center frequency of the ultrasound wave is 5 to 15 MHz. The center frequency can be changed according to setting. The number of elements of the probe is 256. Note that the type, the number, the arrangement, and the like of the elements (oscillators) are not limited to this. For example, a single element may be scanned to measure a wide range or a two-dimensional array oscillator may be used. A configuration in which a plurality of elements are disposed on a bowl-like probe rather than a plane is also desirable.

The ultrasound transmitting unit 102 includes a trigger generating circuit, a delay circuit, and a pulser circuit. The trigger generating circuit determines transmission timing of an ultrasound wave and the like. The delay circuit determines directivity of a transmission beam and the like. The ultrasound receiving unit 103 includes an amplifier circuit, an A/D converter, a delay circuit, and an adder circuit. The amplifier circuit amplifies, in channels, an electric signal deriving from an ultrasound propagating from an object. The A/D converter converts analog electric signals output from the channels of the amplifier circuit into digital electric signals. The delay circuit emphasizes the digital signals according to reception directivity. The adder circuit performs phase regulating addition after weighting an input signal and performing apodization processing of the input signal. According to these kinds of processing, image generation is executed for each pixel or voxel. Generated image data is sent to the ultrasound-signal processing unit 104.

The ultrasound-signal processing unit 104 performs envelope detection processing or the like and obtains a B-Mode image. The image processing unit 105 applies a noise reduction, structure emphasis, contrast adjustment, and the like to the B-Mode image. Further, if necessary, the image processing unit 105 performs interpolation processing and converts the B-Mode image into a B-Mode image having desired pixel resolution and a desired number of pixels. The ultrasound-signal processing unit 104 and the image processing unit 105 can be configured as, for example, a part of an information processing apparatus that functions as processing means 108.

Alternatively, the ultrasound-signal processing unit 104 and the image processing unit 105 may be configured by physically separate circuits. The information processing apparatus operates according to a command of software in which a control method is programmed and executes steps of information processing of the present invention. Further, the information processing apparatus may perform a part of functions of the ultrasound receiving unit 103. The configuration of the processing means 108 is shown in FIG. 1B from the viewpoint of processing contents. The processing means 108 realized by the information processing apparatus includes, as physical or software-like modules, an image generating unit 108a, a region selecting unit 108b, a distribution creating unit 108c, a point-of-interest classifying unit 108d, and a pixel-value determining unit 108e. Combinations and functions of these modules can be changed according to embodiments.

The obtained B-Mode image after the processing is passed to the apparatus control unit 106 and displayed on the image display unit 107. The apparatus control unit 106 sends an instruction for a control start to the ultrasound-transmitting unit 102 and the like. The apparatus control unit 106 receives an instruction from a surgeon via an interface such as a switch or a button for operation, a keyboard, or a mouse. The apparatus control unit 106 can execute a change of parameters of measurement, a start of the measurement, selection of a processing method for images, storage of patient information and images, an analysis of data, and the like on the basis of the instruction.

In the acquisition of an ultrasound image, an examinee takes a position such as a sitting position or a face-up position according to a segment to be measured. The surgeon applies gel for matching of acoustic impedance to an object and arranges the ultrasound probe 101 in a desired position. The surgeon starts measurement and corrects the position of the ultrasound probe 101 while viewing a state of a part to be examined displayed on a display. If an image of a desired region is obtained, the surgeon ends the measurement.

(Image Processing)

The operation of the image processing unit 105 is explained in detail with reference to a flowchart of FIG. 2. The image processing unit 105 mainly performs pre-processing, structure emphasis, and a noise reduction.

In step S1, the image processing unit 105 obtains a B-Mode image from the ultrasound-signal processing unit 104. The image processing unit 105 proceeds to step S2. Note that the B-Mode image may be an intensity image obtained immediately after envelope detection is performed or may be an image of a size displayed by performing interpolation. This processing can be referred to as image generating step.

In step S2, the image processing unit 105 performs the pre-processing. The pre-processing is processing for performing the structure emphasis. The image processing unit 105 performs processing for dividing a structure and noise. The processing is, for example, processing by a sigmoid function often used for contrast adjustment. Consequently, it is possible to increase a difference between a signal and noise.

In step S3, the image processing unit 105 performs the structure emphasis. The processing is separately explained.

In step S4, the image processing unit 105 performs the noise reduction. The image processing unit 105 applies noise reduction processing to the B-Mode image subjected to the structure emphasis. Since the noise reduction is performed after the structure emphasis, information concerning the structure is less easily lost. That is, if the noise reduction is performed first, the structure information is lost. It is sometimes meaningless to emphasize the structure after the structure information is lost. As a filter for the noise reduction, a filter to which an anisotropic diffusion method is applied, a bilateral filter, a Gaussian filter, and the like are suitable.

In step S5, the image processing unit 105 creates image data to be finally displayed on a display. A sigmoid function, a gamma value, or the like is used.

Note that the order and the like of the pre-processing, the structure emphasis, and the noise reduction are not limited to those explained above.

(Structure Emphasis)

Figure 3:
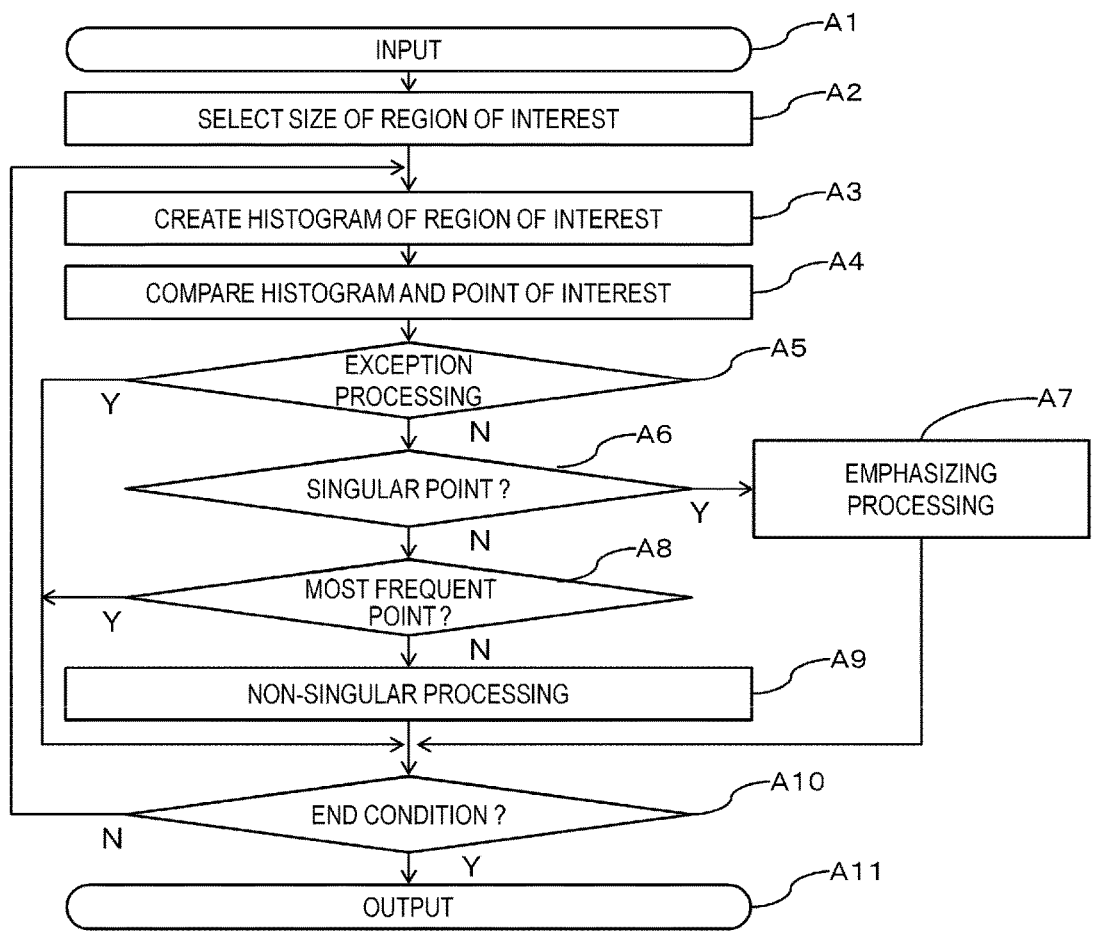
FIG. 3 is a flowchart of structure emphasizing processing in the first embodiment.

Structure emphasizing processing is explained in detail with reference to a flowchart of FIG. 3.

The processing is started in step A1. A state in this step is a state in which an image is input to a structure-emphasizing processing unit.

In step A2, the image processing unit 105 selects a region of interest from the input image. The size of the image input to the structure-emphasizing processing unit is 512×512 pixels. The pixel resolution of an ultrasound image is 0.3 mm both longitudinally and laterally. The size of the region of interest is determined according to the resolution and the frequency of an ultrasound, a position in the depth direction, and the like. The size is pixels×11 pixels. 1 pixel is 10 bits and 1024 gradations. If pixels of numbers 1 to 512 are present in an x direction and pixels of numbers 1 to 512 are present in the depth direction in an image, a range of processing of the image is a range of 6 to 507 in the x direction and 6 to 507 in the depth direction. Note that the size of the region of interest may be set to be different according to a place. For example, in a peripheral section, the size is set to 8 pixels×8 pixels or the like for an increase in speed. This processing can be referred to as region electing step.

In step A3, the image processing unit 105 creates a frequency distribution (a histogram) concerning the brightness of the region of interest. The image processing unit 105 creates a frequency distribution of five stages on the basis of the brightness of 121 pixels included in the 11×11 region of interest centering on a point of interest in the image. The frequency distribution is created in the five stages to provide, in addition to a maximum, a minimum, and a median, which are basic value, sections between the maximum and the median and between the minimum and the median. This makes it possible to execute non-singular processing explained below. Note that, as indicated by Expression (1), width W of the sections is a value obtained by dividing a difference between the maximum and the minimum of the region of interest by 5. This processing can be referred to as distribution creating step.

[Math. 1]

$$W = \frac{ROI_{MX} - ROI_{MN}}{B_{NUM}} \quad (1)$$

In the expression, $ROI_{MX}$ represents the maximum of the region of interest and $ROI_{MN}$ represents the minimum of the region of interest. $B_{NUM}$ represents the number of pins. $B_{NUM}$ is 5.

Figure 4A:
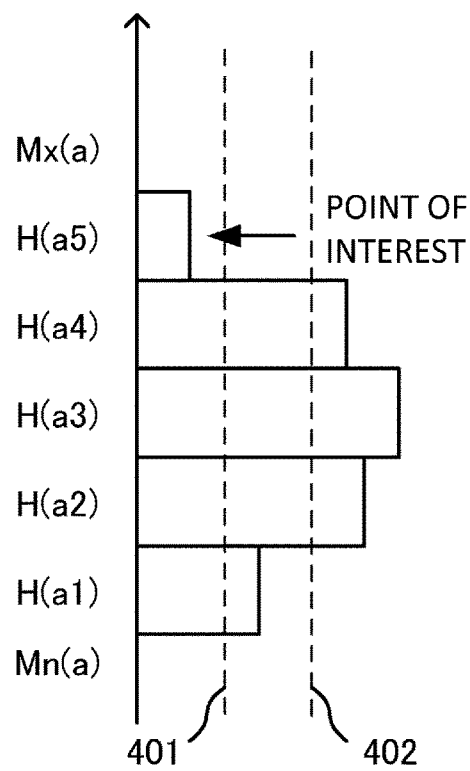
FIGS. 4A and 4B are histogram processing examples in the first embodiment.
Figure 4B:
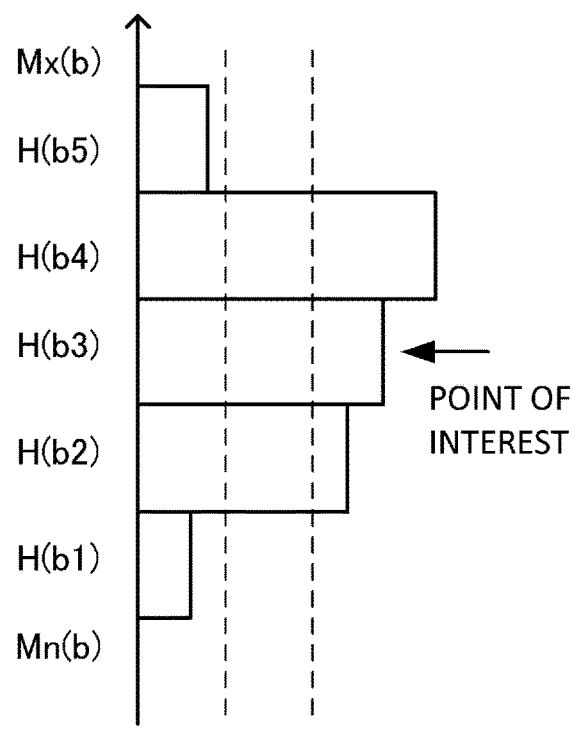

Examples of histograms in which the ordinate is gradation and the abscissa is the number of elements are shown in FIGS. 4A and 4B. In FIG. 4A, the maximum is represented as Mx(a) and the minimum is represented as Mn(a). Five sections are H(a1), H(a2), H(a3), H(a4), and H(a5). In FIG. 4B, the maximum is represented as Mx(b) and the minimum is represented as Mn(b). Five sections are H(b1), H(b2), H(b3), H(b4), and H(b5). In the figures, H(a3) and H(b4) are most frequent sections.

In FIGS. 4A and 4B, a first threshold 401 and a second threshold 402 are respectively present in positions of 1/10 and 1/5 of all elements. The first threshold 401 is used for determination of a singular point. The second threshold 402 is used for determination of a uniform distribution. Note that the frequency distribution may be any distribution as long as the distribution represents a magnitude relation of a relative frequency with respect to the brightness and the intensity of the pixels in the region of interest. For example, the frequency distribution may be standardized as a distribution between 0 and 1. A pixel value may be not only a value after brightness conversion but also an intensity value before the brightness conversion. The pixel value only has to be a value indicating the intensity of a signal of a pixel (a coordinate in the image).

In step A4, the image processing unit 105 compares the histogram and the point of interest. The point of interest in the image is present in H(a5) in FIG. 4A and present in H(b2) in FIG. 4B (respectively indicated by arrows). Processing from this processing to step A8 can be referred to as point-of-interest classifying step. After this step, the point of interest is subjected to various comparison operations. It is determined on the basis of a result of classification of the point of interest whether processing for a pixel value is performed and what is a type of the processing.

The image processing unit 105 performs exception processing in step A5. The exception processing is performed (1) when W is small and (2) when the histogram is uniform. In (1), because of a reason such as absence of a structure or a small signal, since a difference between the maximum and the minimum is small, W is smaller than a predetermined value. In (2), since a region has no characteristic and brightness is uniformly low in the depth direction, a uniformity degree in the sections is high. This determination is performed when there are four sections in 10% near the second threshold. In the case of (1) or (2), the image processing unit 105 proceeds to step A10 without performing any processing. As another example of the exception processing, for example, the histogram is bimodal. In this case as well, the image processing unit 105 proceeds to step A10. In this case, processing for changing the pixel value such as emphasizing processing and non-singular processing is not performed. In the step for performing the exception processing, first determination is performed.

In step A6, the image processing unit 105 determines whether the point of interest is a singular point. The singular point is, for example, a maximum section or a minimum section. The number of elements in the section is equal to or smaller than the first threshold 401. Therefore, in the case of FIG. 4A, it is determined that the point of interest is the singular point. If it is determined that the point of interest is the singular point, the image processing unit 105 performs the emphasizing processing in step A7. If it is determined in step A6 that the point of interest is not the singular point, the image processing unit 105 proceeds to step A8. The step for determining the singular point can be referred to as second determination.

In step A7, the image processing unit 105 performs the emphasizing processing for the point of interest. In the emphasizing processing, for example, when the point of interest is present in the maximum section, the image processing unit 105 adds W/2 to a value of the point of interest to calculate a new value of the point of interest. On the other hand, when the point of interest is present in the minimum section, the image processing unit 105 subtracts W/2 from the value of the point of interest to calculate a new value of the point of interest. After finishing the processing, the image processing unit 105 proceeds to step A9. Naturally, a range of a value that can be taken in the case of 10 bits is 0 to 1023. The processing is performed to keep the value of the point of interest within this region.

In step A8, the image processing unit 105 determines whether the point of interest is a most frequent point. The point of interest is the most frequent point when the point of interest is present in a section where the frequency is the highest (the number of elements is the largest) rather than in the maximum and minimum sections. If it is determined that the point of interest is the most frequent point, the image processing unit 105 proceeds to step A10. If it is determined that the point of interest is not the most frequent point, the image processing unit 105 proceeds to step A9. The step for determining the most frequent point can be referred to as third determination.

In step A9, the image processing unit 105 performs the non-singular processing of the point of interest. The non-singular processing is processing for determining, concerning the point of interest that is neither a characteristic point that should be emphasized nor a point that should be maintained as it is, a pixel value to be close to a general value (e.g., a mode, which is the largest number of elements among the sections). Therefore, if it is determined that the point of interest is none of the exception, the singular point, and the most frequent point, the image processing unit 105 performs the non-singular processing. The image processing unit 105 adds or subtracts W/2 to or from the value of the point of interest to bring the value of the point of interest close to a value of a most frequent point section and calculates a new value.

For example, in the case of FIG. 4B, since the point of interest is a target of non-singular processing, the image processing unit 105 adds W/2 to the value of the point of interest. Note that, in a region of noise, since the value is brought close to the most frequent point by the non-singular processing, an effect of suppressing noise is also displayed. After finishing the processing, the image processing unit 105 proceeds to step A10. The processing from step A5 to this processing can be referred to as pixel-value determining step.

In step A10, the image processing unit 105 determines whether an end condition is met. If the processing in the desired range ends, the image processing unit 105 proceeds to step A11. If the processing in the desired range does not end, the image processing unit 105 returns to step A3 and performs processing of the next point of interest.

In step A11, the structure emphasizing processing ends. The image processing unit 105 outputs an image and proceeds to a noise reducing step.

(Processing Example)

A result of the structure emphasizing processing is shown in the figures. FIGS. 5A and 5B are images of a step structure that simulates a boundary portion of a tumor or the like. A boundary of brightness indicates a boundary of the structure. A state before the processing is shown in an upper figure of FIG. 5A. A state after the processing is shown in a lower figure of FIG. 5A. In FIG. 5B, a cross section of an arrow part of the state before the processing in FIG. 5A is indicated by a dotted line and a cross section of an arrow part of the state after the processing in FIG. 5A is indicated by a solid line. Note that the abscissa indicates a pixel position and the ordinate indicates gradation. A step in the figure is present in a boundary between a position of 40 pixels and a position of 50 pixels. The lines between the positions are slopes. Random noise is added to the entire image.

When the state after the processing (the solid line) and the state before the processing (the dotted line) in FIG. 5B are compared, the solid line is present below the dotted line from 40 pixels to 45 pixels. On the other hand, the solid line is present above the dotted line from 45 pixels to 50 pixels. These are respectively effects of the non-singular processing. That is, a side close to a lower stage is pulled downward and a side close to the upper stage is pulled upward. As a result, the step more sharply stands.

Figures 6A, 6B:
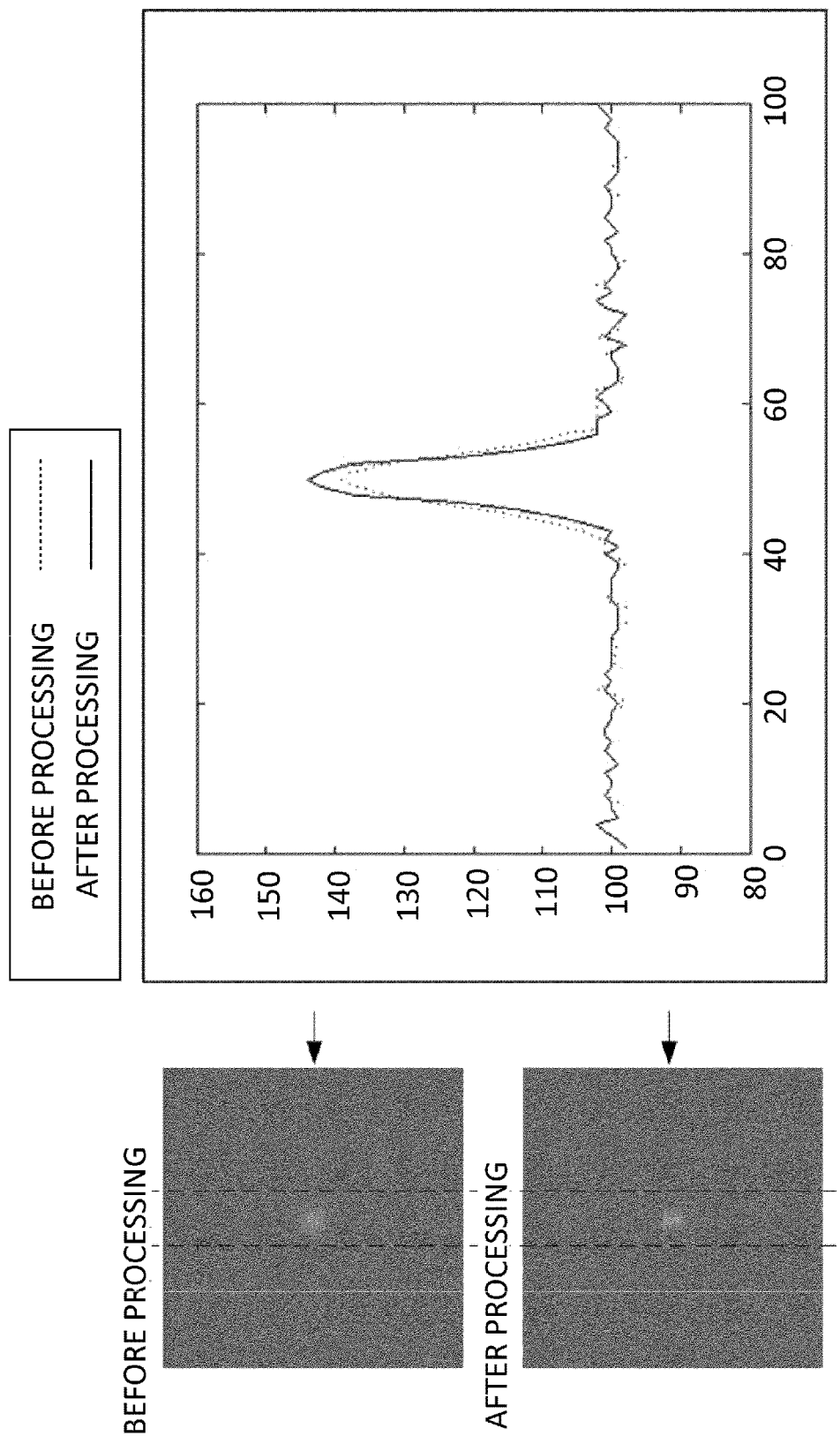
FIGS. 6A and 6B are processing examples of an isolated structure in the first embodiment.

FIGS. 6A and 6B simulate an isolated structure such as a mammary gland. A conical object is present in the center of an image. A state before the processing is shown in an upper figure of FIG. 6A. A state after the processing is shown in a lower figure of FIG. 6A. In FIG. 6B, a cross section of an arrow part of the state before the processing in FIG. 6A is indicated by a dotted line and a cross section of an arrow part of the state after the processing in FIG. 6A is indicated by a solid line.

When the state after the processing (the solid line) and the state before the processing (the dotted line) in FIG. 6B are compared, the solid line is below the dotted line from 45 pixels to 50 pixels. This results from an effect of the non-singular processing as exhibited also in FIG. 5B. Meanwhile, the solid line is above the dotted line from 45 pixels to 50 pixels, and similarly, the solid line is above the dotted line from 50 pixels to 55 pixels. This results from an effect of the emphasizing processing of the singular point. The solid line is present below the dotted line from 55 pixels to 60 pixels. An effect of the non-singular processing appears.

Note that a region of only noise is made flat by the non-singular processing. Therefore, the noise is smaller.

Note that the above explanation is based on the premise that the image is a monochrome image. However, the image may be a color image of Doppler measurement or elastography. For example, if the intensity corresponds to color as one variable, the processing explained above is performed to replace the intensity with the corresponding color. If the intensity is three variables of RGB, the processing explained above only has to be performed in the respective colors.

As explained above, according to the structure emphasizing processing in this embodiment, it is possible to steepen the step and emphasize the isolated structure. As a result, the structure is emphasized with respect to the noise.

Second Embodiment

An ultrasound diagnostic apparatus according to a second embodiment can obtain a three-dimensional image by two-dimensionally scanning an ultrasound probe.

(Apparatus)

Figures 7A, 7B:
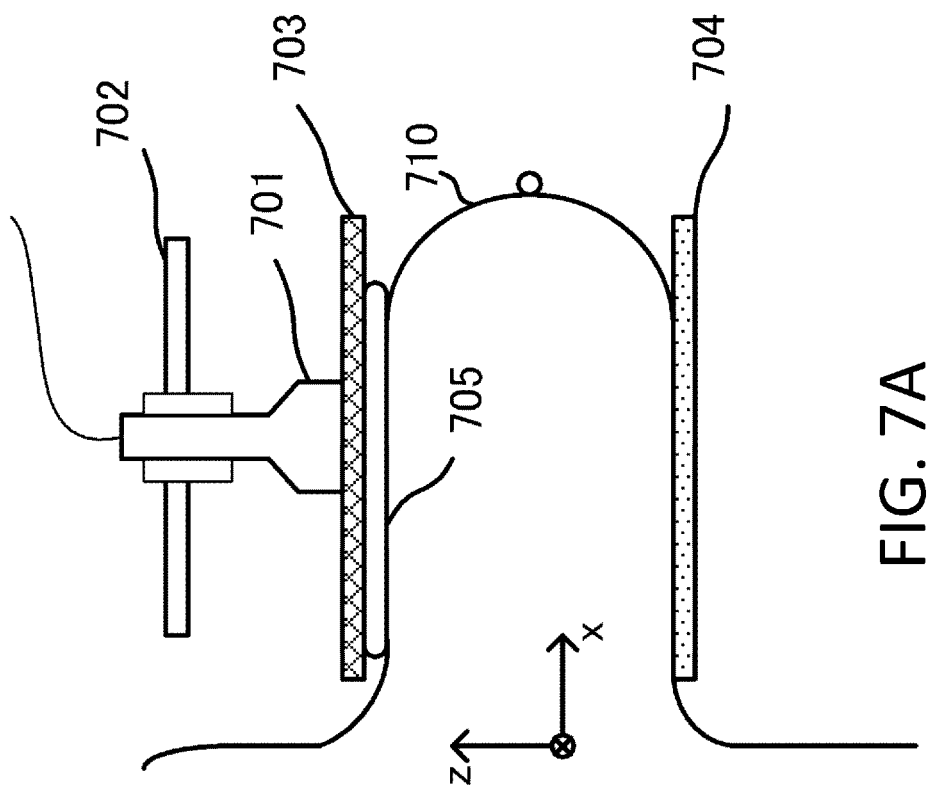
FIGS. 7A and 7B are diagrams of a three-dimensional ultrasound diagnostic apparatus in a second embodiment.

A schematic diagram of the ultrasound diagnostic apparatus is shown in FIGS. 7A and 7B. The apparatus performs ultrasound measurement in a state in which a breast 710 is held between holding plates 703 and 704.

Specifically, an examinee in a standing position or a sitting position inserts the breast 710 into between the holding plates 703 and 704. The breast 710 is held by the holding plates 703 and 704. The material of the holding plates 703 and 704 is desirably a material that easily transmits an ultrasound wave. Typically, a glass material, acryl, polymethylpentene, epoxy resin, and the like are suitable. It is preferable to provide an acoustic matching layer 705.

An ultrasound probe 701 transmits an ultrasound wave to an object via the holding plate 703. The ultrasound wave reflected on the object returns to the ultrasound probe 701 via the holding plate 703.

The ultrasound probe 701 scans, with a scanning mechanism 702, the holding plate 703 on an xy plane and obtains a three-dimensional ultrasound image. A schematic diagram of a scanning pattern is shown in FIG. 7B. The ultrasound probe 701 performs the scanning in a y direction parallel to a line that connects the shoulders. At this point, the y direction is parallel to an elevation direction. When performing the scanning in the y direction, the ultrasound probe 701 transmits and receives ultrasound waves to acquire an image. Control of the scanning mechanism 702 is performed by the apparatus control unit 106. Note that setting of the x, y, and z directions with respect to the position of the examinee is not limited to this. A direction in which the breast is held and a holding member are not limited to the above. For example, a cup-like holding member rather than a flat holding member may be used.

The obtained image is processed by the ultrasound-signal processing unit 104 and sent to the image processing unit 105. The image processing unit 105 reconfigures the image from a position on the xy plane and obtains a three-dimensional ultrasound image. The image processing unit 105 obtains a final image by applying image processing to the three-dimensional ultrasound image. In the image processing, as in the first embodiment, the image processing unit 105 performs pre-processing, structure emphasis, and a noise reduction using three-dimensional data. Note that the three-dimensional data is formed of the pixels of numbers 1 to 512 with respect to each of x, y, and z axes.

In the structure emphasis, sizes of a region of interest are determined in the x, y, and z directions on the basis of the resolution of pixels. For example, when the resolution is 0.3 mm in all of the x, y, and z directions, the region of interest is 7×7×7 pixels centering on a point of interest. Therefore, if resolutions are different in the respective x, y, and z directions, the number of pixels may be selected according to the resolutions such that the region have approximately the same length in the directions. A histogram is created from the three-dimensional data using a pixel value of the selected pixels. This range is a region of the pixels of numbers 6 to 507 in all of the x, y, and z directions.

As explained above, according to this embodiment, concerning a three-dimensional region of interest, image processing can be performed using a large number of data present at a near distance from the point of interest. As in the first embodiment, it is possible to execute singular point emphasizing processing, non-singular processing, and the like by performing, according to a situation of a histogram and the position of a point of interest in the histogram, an arithmetic operation for a pixel value of the point of interest. As a result, it is possible to generate three-dimensional image data with speckle noise suppressed while emphasizing a structure. Therefore, it is possible to realize satisfactory ultrasound diagnosis.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-120292, filed on Jun. 11, 2014, which is hereby incorporated by reference wherein in its entirety.

What is claimed is:

1. An object information acquiring apparatus comprising:
a processor that obtains an image of an inside of an object generated by using an electric signal obtained by receiving an acoustic wave propagating from the object,
wherein the processor:
creates a frequency distribution of pixel values included in a region of interest including a point of interest in the image, the frequency distribution being expressed by a plurality of sections and a number of elements having a pixel value included in each of the plurality of sections,
determines, from among the plurality of sections, a section which includes a pixel value of the point of interest, and
changes a process for the pixel value of the point of interest on the basis of the section which includes the pixel value of the point of interest,
wherein, in a case where the pixel value of the point of interest is included in a maximum section or a minimum section among the plurality of sections, the processor performs an emphasizing processing on the pixel value of the point of interest, and
wherein, in a case where the pixel value of the point of interest is not included in either the maximum section, the minimum section or a section of a most frequent point among the plurality of sections, the processor performs a non-singular processing on the pixel value of the point of interest such that the pixel value of the point of interest is close to a mode of the frequency distribution.

2. The object information acquiring apparatus according to claim 1, wherein the processor determines a size of the region of interest according to a frequency of the acoustic wave.

3. The object information acquiring apparatus according to claim 1, wherein the processor determines a size of the region of interest according to a position of the point of interest in the image.

4. The object information acquiring apparatus according to claim 1, wherein the processor does not change the pixel value of the point of interest in a case where a difference between a maximum value and a minimum value of the frequency distribution is smaller than a predetermined value.

5. The object information acquiring apparatus according to claim 1, wherein the processor does not change the pixel value of the point of interest in a case where the frequency distribution is uniform.

6. The object information acquiring apparatus according to claim 1, wherein the processor adds a predetermined value to the pixel value of the point of interest in a case that the pixel value of the point of interest is included in the maximum section among the plurality of sections and subtracts a predetermined value from the pixel value of the point of interest in a case that the pixel value of the point of interest is included in the minimum section among the plurality of sections.

7. The object information acquiring apparatus according to claim 1, wherein the processor does not change the pixel value of the point of interest in a case where the number of elements of the section which includes the pixel value of the point of interest is largest among the plurality of sections.

8. The object information acquiring apparatus according to claim 1, further comprising an ultrasound probe that receives the acoustic wave propagating from the object and outputs the electric signal.

9. The object information acquiring apparatus according to claim 1, wherein the processor performs, for each of a plurality of points of interest in the image, a determination of a section which includes a pixel value of a point of interest from among the plurality of sections and a determination of a process for the pixel value of the point of interest of each of the plurality of points.

10. An image processing method comprising:
an image obtaining step for obtaining an image of an inside of an object generated by using an electric signal obtained by receiving an acoustic wave propagating from the object;
a distribution creating step for creating a frequency distribution of pixel values included in a region of interest including a point of interest in the image, the frequency distribution being expressed by a plurality of sections and a number of elements having a pixel value included in each of the plurality of sections;
a section determining step for determining, from among the plurality of sections, a section which includes a pixel value of the point of interest; and
a process changing step for changing a process for the pixel value of the point of interest on the basis of the section which includes the pixel value of the point of interest,
wherein, in a case where the pixel value of the point of interest is included in a maximum section or a minimum section among the plurality of sections, emphasizing processing is performed on the pixel value of the point of interest, and
wherein, in a case where the pixel value of the point of interest is not included in either the maximum section, the minimum section or a section of a most frequent point among the plurality of sections, non-singular processing is performed on the pixel value of the point of interest such that the pixel value of the point of interest is close to a mode of the frequency distribution.

11. A non-transitory computer-readable medium that stores a program, wherein the program causes a computer to execute:
an image obtaining step for obtaining an image of an inside of an object generated by using an electric signal obtained by receiving an acoustic wave propagating from the object;
a distribution creating step for creating a frequency distribution of pixel values included in a region of interest including a point of interest in the image, the frequency distribution being expressed by a plurality of sections and a number of elements having a pixel value included in each of the plurality of sections;
a section determining step for determining, from among the plurality of sections, a section which includes a pixel value of the point of interest; and
a process changing step for changing a process for the pixel value of the point of interest on the basis of the section which includes the pixel value of the point of interest,
wherein, in a case where the pixel value of the point of interest is included in a maximum section or a minimum section among the plurality of sections, the computer performs an emphasizing processing on the pixel value of the point of interest, and
wherein, in a case where the pixel value of the point of interest is not included in either the maximum section, the minimum section or a section of a most frequent point among the plurality of sections, the computer performs a non-singular processing on the pixel value of the point of interest such that the pixel value of the point of interest is close to a mode of the frequency distribution.

\* \* \* \* \*